(12) United States Patent
Van der Putten

(10) Patent No.: US 6,566,580 B1
(45) Date of Patent: May 20, 2003

(54) NEUROLOGICAL DISEASE MODEL

(75) Inventor: Petrus Herman Maria Van der Putten, Binningen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/254,524

(22) PCT Filed: Sep. 11, 1997

(86) PCT No.: PCT/EP97/04985

§ 371 (c)(1),
(2), (4) Date: Mar. 8, 1999

(87) PCT Pub. No.: WO98/11242

PCT Pub. Date: Mar. 19, 1998

(30) Foreign Application Priority Data

Sep. 13, 1996 (EP) .............................................. 96114717

(51) Int. Cl.$^7$ ........................ G01N 33/00; A01K 67/00; A01K 67/033; A01K 67/027

(52) U.S. Cl. ............................... 800/3; 800/13; 800/14; 800/18; 800/8; 800/9

(58) Field of Search .............................. 800/21, 3, 8, 9, 800/18, 14; 514/44; 435/440, 449

(56) References Cited

FOREIGN PATENT DOCUMENTS

| WO | 95/08627 | 3/1995 |
|---|---|---|
| WO | 95 18154 | 7/1995 |

OTHER PUBLICATIONS

F Shalaby et al., Nature, "Failure of blood–island formation anf vasculogenesis in Flk–1–deficient mice," Jul. 1995, vol. 376, pp. 62–70.*

CD Sigmund, Arterioscler Thromb Vasc Biol., "Viewpoint: Are Studies in Genetically Altered Mice Out of Control!" 2000, 20:1425–1429.*

CB Moena, Development, "Defects in heart and lung development in compound heterozygotes for two different targeted mutations at the N–myc locus," 1991,pp. 485–499.*

K.H.S. Campbell et al., Theriogenology,"Totipotency or multiipotentiality of cultured cells: Applications and Progress,"Jan. 1997, vol. 47, Issue 1, pp. 63–72.*

A. Bradley et al., Bio/Technology, "Modifying the mouse:Design and desire," May 1992, vol. 10, pp. 534–539.*

W. French Anderson. Human gene therapy. Nature, vol. 392, pp. 25–30. 1998.*

Ilyin et al. Pharmacology of ACEA–1416: a potent systemically actice NMDA receptor glycine site antagonist. European Journal of Pharmacology. vol. 310, pp. 107–114. 1996.*

Tizzano et al. Induction of protection of limbic seizures in mice by mGluR subtype selective agonists. Neuropharmacology. vol. 34, No. 8, pp. 1063–1067. 1995.*

F. Conquet. Inactivation in vivo of metabotropic glutamate receptor 1 by specific chromosomal insertion of reporter gene lacZ. Neuropharmacology. vol. 34, No. 8, pp. 865–870. 1995.*

Ronald G. Crystal. Transfer of genes to humans: early lessons and obstacles to success. Science, vol. 270, pp. 404–410, 1995.*

Suzuki et al. Anticonvulsant action of metabotropic glutamate receptor agonists in kindled amygdala of rats. Neuroscience Letters, vol. 204, pp. 41–44, 1996.*

Tizzano et al. Intracerebral 1s, 3R–1 aminocyclopentane–1, 3–dicarboxylic acid(1s,3R–acpd) produces limbic seizures that are not blocked by ionotropic glutamate receptor antagonists. Neuroscience Lett. 162, 12–16, 1993.*

Brandstätter et al., Journal of Neuroscience, vol. 16(15), "Compartmental Localization of Metabotropic Glutamate Receptor (mGluR7): Two Different Active Sites at a Retinal Synapse," pp. 4749–4756 (1996).

Capecchi M.R., Science, vol. 244, "Altering the Genome by Homologous Recombination," pp. 1288–1292 (1989).

Conquet F., Neuropharmacology, vol. 34(8), "Inactivation In Vivo of Metabotropic Glutamate Receptor 1 by Specific Chromosomal Insertion of Reporter Gene lacZ," pp. 865–870 (1995).

Flor et al., Neuropharmacology, vol. 36(2), "A Novel Splice Variant of a Metabotropic Glutamate Receptor, Human mGluR7b," pp. 153–159 (1997).

Gereau and Conn, Journal of Neuroscience, vol. 15(10), "Multiple Presynaptic Metabotropic Glutamate Receptors Modulate Excitatory and Inhibitory Synaptic Transmission in Hippocampal Area CA1," pp. 6879–6889 (1995).

Hanse and Gustafsson, Neuroscience Research, vol. 20, "Onset and stabilization of NMDA receptor–dependent hippocampal long–term potentiation," pp. 15–25 (1994).

Mansour et al., Nature, vol. 336(24), "Disruption of the proto–oncogene int–2 in mouse embryo–derived stem cells: a general strategy for targeting mutations to non–selectable genes," pp. 348–352 (1988).

Manzoni and Bockaert, European Journal of Neuroscience, vol. 7, "Metabotropic Glutamate Receptors Inhibiting Excitatory Synapses in the CA1 Area of Rat Hippocampus," pp. 2518–2523 (1995).

(List continued on next page.)

*Primary Examiner*—Anne-Marie Baker
(74) *Attorney, Agent, or Firm*—Hesna J. Pfeiffer

(57) ABSTRACT

The use of a metabotropic glutamate receptor mGluR7 agonist for the facilitation of neurotransmitter release from a nerve ending and the treatment of neurological conditions, including epilepsy. Transgenic knockout non-human mammals are provided which lack the mGluR7 gene, suitable for studying mGluR7 and modulators thereof as well as epilepsy. Specifically provided is a transgenic mouse homozygous for an inactivated endogenous mGlu7 gene which exhibits symptoms of epileptic seizures.

4 Claims, 1 Drawing Sheet

OTHER PUBLICATIONS

Ohishi et al., Neuroscience Letters, vol. 202, "Presynaptic localization of a metabotropic glutamate receptor, mGluR7, in the primary afferent neurons: an immunohistochemical study in the rat," pp. 85–88 (1995).

Okamoto et al., Journal of Biological Chemistry, vol. 269(2), "Molecular Characterization of a New Metabotropic Glutamate Receptor mGluR7 Coupled to Inhibitory Cyclic AMP Signal Transduction," pp. 1231–1236 (1994).

Saugstad et al., Molecular Pharmacology, vol. 45, "Cloning and Expression of a New Member of the L–2–Amino–4–phosphonobutyric Acid–Sensitive Class of Metabotropic Glutamate Receptors," pp. 367–372 (1993).

Shigemoto et al., Nature, vol. 381, "Target–cell–specific concentration of a metabotropic glutamate receptor in the presynaptic active zone," pp. 523–525 (1996).

* cited by examiner

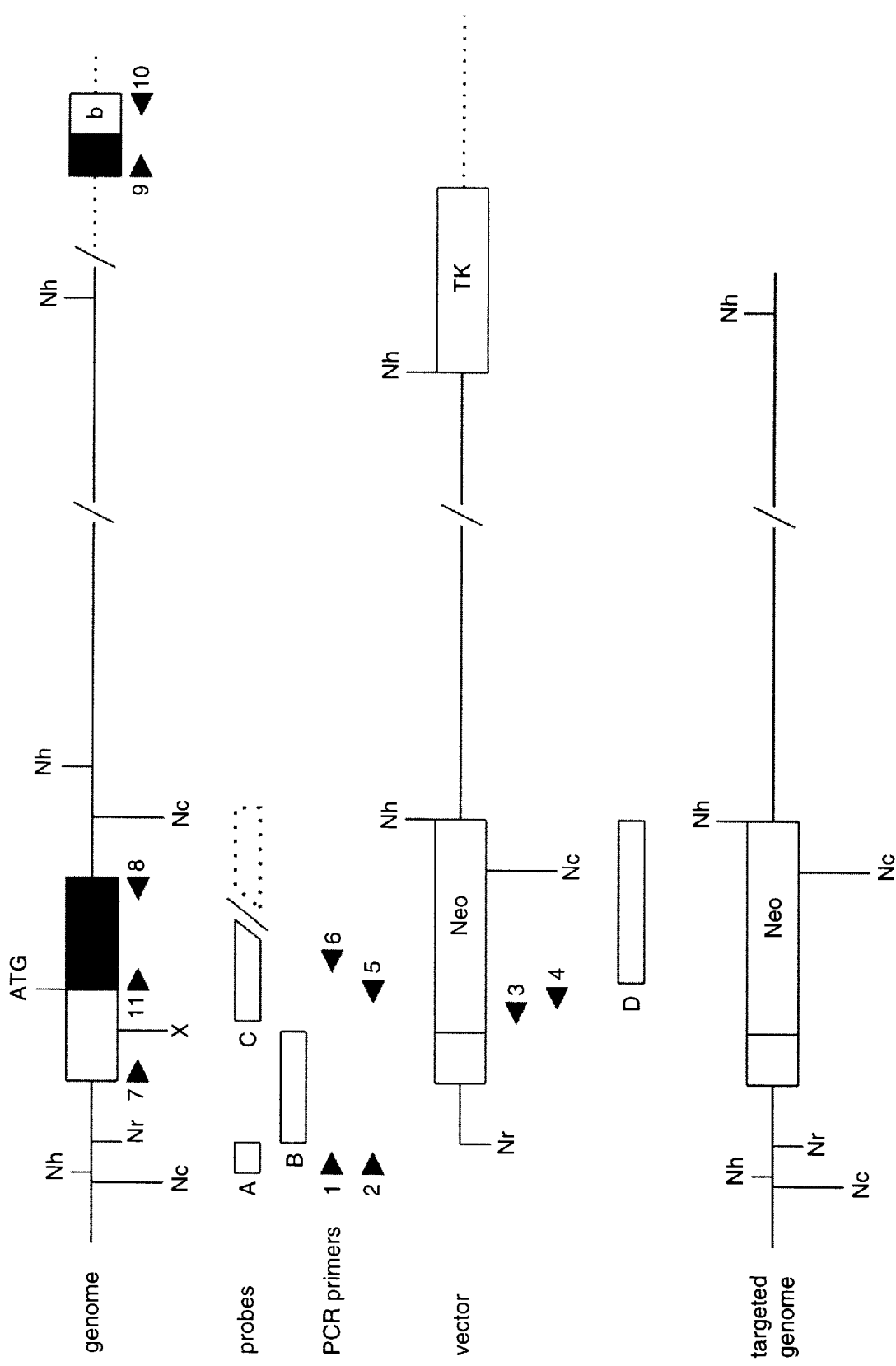

SEQUENCE LISTING

```
<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 1
cttctgccag agctgacagt caaag                                       25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 2
gtcagcacca atatcgcgac tcatc                                       25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 3
```

-continued

```
<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 4
gcgctgacag ccggaacacg                                                    20

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:PCR primer

<400> SEQUENCE: 5
gaaagtgagc gactgttcga gcg                                                23

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:PCR primer

<400> SEQUENCE: 6
gatgttggct accatgatgg agaccg                                             26

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 7
gagagatgga tagcaagcaa gggag                                              25

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:PCR primer

<400> SEQUENCE: 8
gtgtccctgg aacaagtgtc cag                                                23
```

(first line, continued from previous page:)

```
gcgtgcaatc catcttgttc aatgg                                              25
```

NEUROLOGICAL DISEASE MODEL

This is a national stage of International Application Ser. No. PCT/EP97/04985, filed Sep. 11, 1997.

The present invention relates to metabotropic glutamate receptors (mGluRs). In particular, the invention relates to the mGlu₇ receptor and novel applications thereof in models for neurological disease and as a target for neuroactive drugs.

L-glutamate is the major excitatory neurotransmitter in the central nervous system (CNS). Two major classes of glutamatergic receptors exist. The first class, the ionotropic receptors, which consists of NMDA, AMPA and kainate receptors, is responsible for fast synaptic transmission in the mammalian CNS. The second class, the metabotropic glutamate receptors (mGluR), exert actions on neurotransmission, synaptic plasticity and cellular excitation that are less well characterised.

Synaptic release of neurotransmitter in the nervous system is often influenced by presynaptic mGluRs which in turn respond to neurotransmitters released from the same nerve terminal or from terminals of other neurons. The mGluRs have diverse critical roles in forms of synaptic plasticity such as long term potentiation (LTP) or long term depression, forms of synaptic plasticity believed to be involved in learning and memory in vertebrates. Presynaptic mGluR autoreceptors respond to glutamate and influence the probability of neurotransmitter release from a nerve terminal. In general, the activation of presynaptic mGluRs (e.g. class III mGluRs activated by L-AP4), has been found to reduce transmitter release from synapses in many brain regions.

One member of the mGluR family, mGluR7, has been only poorly characterised to date. It is the most conserved member of the mGluR family, with only 6–8 amino acid differences observed between rat and human proteins. mGluR7 is widely distributed throughout the nervous system and is localised presynaptically close to neurotransmitter release sites. In the hippocampus, a high density of the mGlu₇a isoform (note: to date only two isoforms of mGluR7, a and b, that differ only in their carboxy-terminal amino acid sequence have been characterized; Flor, P. J., van der Putten, H., Ruegg, D., Lukic, S., Leonhardt, T., Sansig, G., Knoepfel, T., and Kuhn, R. 1996. A novel splice variant of a metabotropic glutamate receptor, human mGluR7b; *Neuropharmacology* 36, 153–159) is found, in particular, in presynaptic terminals of excitatory cells that synapse on mGluR1α expressing GABA-ergic interneurons that also express somatostatin. Therefore, the input of this particular class of interneuron seems to be endowed by a particularly strong mGluR7-mediated autoregulation. Why this is so remains speculative for the moment and it has been suggested that this peculiar mGluR7-mediated autoregulation might relate to the role of the mGluR1α₁-positive interneurons in the hippocampal network (Shigemoto et al., Nature (1996) 318:523–525). mGluR1α⁺ cells receive glutamatergic input from axon collaterals of principal cells. The GABAergic terminals of mGluR1α⁺ cells make synapses on principal cell distal dendrites, which also receive a direct excitatory input from the entorhinal cortex.

It has been hitherto generally accepted and shown that the glutamate analogue (S)-2-amino-4-phosphonobutanoate (L-AP4) induced presynaptic suppression of neurotransmitter release. In several instances, it has been proposed that such an effect could be mediated by activation of mGluR7 receptors. In other words, it has been proposed that activation of mGluR7 results in inhibition of neurotransmitter release. Building on this presumption, Shigemoto et al. (Op. Cit.) suggest that the high level of presynaptic mGluR7 may suppress the release of glutamate when action potentials arrive at high frequency, allowing glutamate release to follow only relatively low frequency synaptic firing. According to this hypothesis mGluR7 would work as a low pass filter and its gating function would allow low but not high frequency stimuli to be passed on effectively. This has implications for the use of glutamate agonists and/or antagonists in the therapy of disorders associated with synaptic plasticity, such as learning and memory disorders, epilepsy, pain and possibly ischaemia. According to the generally accepted model, a mGluR7 agonist would be effective in reducing transmitter release and a mGluR7 agonist would have more pronounced-effects on transmitter release in terminals that are particularly enriched in mGluR7 such as excitatory terminals onto mGluR1α⁺ interneurons. Also, according to data and models proposed, so far, agonists of mGluR7 would have more pronounced inhibitory effects on excitatory terminals that release transmitter to interneurons. This would favour a decrease in inhibition exerted by the interneurons. Agonists of mGluR7 might therefore lower rather than enhance thresholds for seizures and epilepsy caused by decreased inhibition. Current models thus favour the development of antagonists rather than agonists of mGluR7 for the treatment of diseases such as epilepsy or relieving symptoms related to a reduction of neurotransmitter release.

We have used knockout mice in which the mGluR7 gene has been deleted in order to determine that this hypothesis and its implications are incorrect. mGluR7 facilitates rather than inhibiting glutamate release.

SUMMARY OF THE INVENTION

The present invention provides the use of a metabotropic glutamate receptor mGluR7 agonist for the facilitation of neurotransmitter release from a nerve ending. Moreover, the invention.provides transgenic knockout non-human mammals lacking the mGluR7 gene, suitable for studying mGluR7 and modulators thereof. Furthermore, the transgenic knockout mammals according to the invention are suitable for the study of epilepsy.

BRIEF DESCRIPTION OF THE DRAWING

FIG. 1 is a schematic representation of the mouse mGluR7 gene showing the points of insertion of the disrupting nucleic acid sequence and the location of the PCR probes described in the text.

DETAILED DESCRIPTION OF THE INVENTION

The unchallenged presumption existing in the art hitherto has been that activation of mGluR7 is responsible for inhibition of neurotransmitter release from nerve endings in response to glutamate. Data from mGluR7 knockout (−/−) mice indicate, however, that mGluR7 has a facilitatory role in synaptic transmission, a role contrary to the hypothetical role put forward by Shigemoto et al. (Op. Cit.) and all literature published so far relating the function on mGluR7 and the use of mGluR class III specific agonists or antagonists.

Activation of mGluR7 by glutamate or an analogue thereof results in the facilitation of neurotransmitter release from the presynaptic nerve ending, and thus a stimulation of nerve signalling. Conversely, inactivity of mGluR7 leads to reduced presynaptic neurotransmitter release and thus a reduction in nerve signalling. This has been determined using transgenic knockout mice lacking mGluR7, and accordingly the invention provides a transgenic non-human mammal in which the mGluR7 gene has been deleted. In accordance with the invention, therefore, there is provided the use of mGluR7 antagonists to reduce neurotransmitter release.

The structures of mGluR7 and of nucleic acids encoding mGluR7 are known, for example from published European Patent Application 0 720 650 (Ciba-Geigy AG) and Okamoto et al., (1994) J. Biol. Chem. 269:1231–1236. Techniques for deleting the $mGlu_7$ gene from the genome of transgenic mammals are also known, and typically involve gene deletion by homologous recombination (Capecchi, M. R., (1989) Science 244:1288–1292) in pluripotent embryonic stem (ES) cells, which are subsequently inserted into developing early stage mouse embryos in order to give rise to chimeric transgenic animals (Mansour et al., (1989) Nature 336, 348–352). Pure transgenic animals may then be obtained by selective breeding. The transgenic non-human mammal of the invention is therefore preferably a mouse. Gene deletion is advantageously accomplished by insertion of a nucleic acid element into the endogenous gene, thereby disrupting its expression at the transcriptional and/or translational levels.

Transgenic animals according to the invention are useful for the further study of the biological role of mGluR7 in the nervous system. For example, it is to be expected that mGluR7 in presynaptic terminals of glutamatergic cells synapsing onto inhibitory interneurons would increase excitation of interneurons thereby facilitating inhibition. This principle should hold for $mGluR1\alpha^+$ interneurons in the hippocampus and all other presynaptic glutamatergic terminals in the brain that contain mGluR7 and that synapse onto inhibitory cells. The presence of mGluR7 in such terminals is a common feature in the nervous system (Shigemoto et al., Op. Cit.; Brandstetter et al., (1996) J. Neurosci., 16:4749–4756). Accordingly, one would expect a decrease in GABAergic interneuron-mediated inhibition in mice lacking a functional mGluR7 gene. As a result, we predict a lower threshold for spontaneous or evoked seizure activity in mGluR7 knockout mice as compared to mice carrying a functional mGluR7 gene. Using knockout mice according to the invention, it has been observed that this is in fact what happens. mGluR7−/− mice, in contrast to their wild-type littermates or littermates carrying only one of the two mGluR7 alleles disrupted, develop spontaneous seizures as a result of sensory stimulation, for example when transferred to a new cage. The epileptic phenotype becomes detectable at around three months of age and is sex-independent. When seizures occur, mGluR7 knockout mice show clonic-like seizures of varying severity, sometimes accompanied by running. Seizure periods are usually followed by a lag phase of one to several days before the next seizure can be triggered (see Example 3). Knockout mice may therefore be used as a means to screen agents for their potential anti-epileptic properties, with a reduction in frequency or intensity of the seizures being indicative of anti-epileptic activity. Seizures may be triggered, for example, by sensory stimulation, electrically or chemically. The invention accordingly provides the use of mGluR7 knockout mice for the study of epilepsy.

Compounds identified according to the invention are useful for the treatment of epilepsy. It is the surprising determination of the present invention that mGluR7 facilitates neurotransmission. But, notwithstanding this finding, it is also the case that mGluR7 modulators (agonists, partial agonists, or antagonists) are predicted to be effective in treating epilepsy. The reason for this is believed to be that mGluR7 activity (hence also agonists of mGluR7) in neurons synapsing onto inhibitory neurons is responsible for the downregulation of excess neural stimulation. Thus, mGluR7 activity, by facilitating neurotransmitter release and increasing inhibitory neuron stimulation, is predicted to have inhibitory effects on excitation thereby increasing thresholds allowing the initiation and/or propagation of epileptic seizures. The invention accordingly provides the use of an agent which modulates neurotransmitter release as a result of its action on mGluR7 for the manufacture of a composition for the treatment of seizures. Preferably, the agent is an mGluR7 agonist. Moreover, the invention in broad terms provides the use of mGluR7 agonists for facilitating neurotransmitter release from a nerve ending, as well as the use of mGluR7 antagonists for inhibiting neurotransmitter release from a nerve ending. For example, the invention accordingly provides the use of mGluR7 antagonists for the inhibition of signalling at such synapses and thus the therapy of pain conditions. Some axon terminals of the primary afferent fibers to laminae I and II of the dorsal horn are provided with mGluR7 (Ohishi et al., (1995) Neurosci. Lett., 202:85–88). These fibers are involved in pain transmission.

Further experiments, for example involving administration of agents such as isoniazid or metrazol (see Example 4), may be designed in order to investigate the biological role of mGluR7 and agonists, antagonists or partial agonists of mGluR7, in epilepsy. In a preferred aspect, such experiments may be performed in double transgenic animals, that is animals which lack one or both of the mGluR7 alleles and in addition have been transformed with a heterologous gene or had one gene other than mGluR7 knocked out. The heterologous gene may be unrelated to mGluR7, a mGluR7 gene from another species (e.g. human), a single isoform of mGluR7, or may be a mutated form thereof. In a specific embodiment, the mutated form may be a conditional mGluR7 gene which may be switched on or off at will. State-of-the-art transgene technology allows the construction of such animal models. For example, transgenes can be constructed that will express in all or subsets of $mGluR7^+$ neurons, a constitutive or modulatable form of the phage P1 Cre recombinase, equipped with a nuclear targeting signal allowing the protein to enter the nucleus of postmitotic cells. Commonly, modulatable forms of Cre are and have been generated e.g. as fusion molecules containing Cre recombinase with an amino- as well as a carboxy-terminal extension comprised of a hormone binding domain (HBD) derived from a mutant oestrogen receptor that only responds to tamoxifen. By in vivo administration of such a small molecule, foreign to the mammal, a transgene-expressed enzymatically inactive HBD-Cre-HBD fusion protein can be activated in mice that contain a modified endogenous mGluR7 gene harbouring phage P1 Cre-specific recognition and recombination sites (lox-sites). The combination may be carried out conveniently by crossing mGluR7 lox mice (generated using state-of-the-art homologous recombination technology in embryonic stem cells) with mice transgenic for HBD-Cre-HBD in order to obtain double transformants. Moreover, targeted delivery of Cre could also be achieved using vectors such as adenoviral vectors carrying a promoter-Cre construct which expresses Cre in a tissue and cell-type specific manner may be used to specifically ablate mGluR7 in brain regions. Such an approach serves to generate focal models for epilepsy.

In an alternative aspect of the present invention, there is provided a method for identifying a compound or mixture of compounds which is able to facilitate neurotransmitter release from a nerve ending comprising assessing whether the compound or group of compounds is an mGlu$_7$ agonist, as well as a method for identifying a compound or mixture of compounds which is able to inhibit neurotransmitter release from a nerve ending comprising assessing whether the compound or group of compounds is an mGluR7 antagonist.

Methods for assessing whether agents are agonists or antagonists of mGluR7 are provided by the present invention. mGluR7 knockout mice and non-transgenic or heterozygous littermates may be used in comparative assays in order to determine those agents which display activity in non-transgenic mice but not in mGluR7 knockouts. The invention thus provides a method for the identification of specific mGlu$_7$ agonists and antagonists.

The effect on mGluR7−/− mice monitored in this system may be a behavioural effect, preferably manifesting itself in a modulation of the animal's susceptibility to epileptic seizure, of a biological effect, preferably measurable by electrophysiological measurement of neural activity. The behavioural approach has the advantage of being readily implementable with the minimum of equipment, requiring only observation of mouse populations. The electrophysiological approach is more complex, requiring surgical procedures in order to measure neural activity, but should be faster and easier to score than behavioural observation.

Alternative screening systems, whether cell-based or in vitro, can be designed by those skilled in the art. It should be noted, however, that certain cell-based systems have in the past provided results which are not consistent with the results obtained in vivo in mGluR7−/− mice. Both Okamoto et al., *op. cit.*, and Saugstad et al., (1994) Mol. Pharmacol. 45:367–372 report apparent inhibition of neurotransmitter release by the class III mGluR agonist L-AP4. As set forth herein, such results are not reflected with the activity of mGluR7, in that it appears almost completely insensitive to L-AP4 and when stimulated acts as a facilitator, not an inhibitor, of neurotransmitter release.

Preferably, therefore, alternative screening systems according to the invention are carried out in an environment which functionally mimics an in vivo system. For example, tissue slices in organ culture may be used in order to generate electrophysiological readings or other data. Alternatively, it may be possible to use tissue culture techniques, for example with neural cells, which maintain functional fidelity to the in vivo system.

In preferred embodiments of alternative screening systems, mGluR7 encoding DNA is ligated into a vector, and introduced into suitable host cells to produce transformed cell lines that express mGluR7. The resulting transformed cells may be in the form of tissue slices or primary cell culture, or preferably in the form of cell lines which can then be reproduced for reproducible qualitative and/or quantitative analysis of the effect(s) of potential drugs affecting mGluR7 function. Thus mGluR7 expressing cells may be employed for the identification of compounds, particularly small molecular weight compounds, which modulate the function of mGluR7. Host cells expressing mGluR7 are useful for drug screening and it is a further object of the present invention to provide a method for identifying compounds which modulate the activity of mGluR7, said method comprising exposing cells containing heterologous DNA encoding mGluR7, wherein said cells produce functional mGluR7, to at least one compound or mixture of compounds or signal whose ability to modulate the activity of said mGluR7 is sought to be determined, and thereafter monitoring said cells for changes caused by said modulation. Such an assay enables the identification of modulators, such as agonists, antagonists and allosteric modulators, of mGluR7. As used herein, a compound or signal that modulates the activity of mGlu$_7$ refers to a compound that alters the activity of mGlu$_7$ in such a way that the activity of mGlu$_7$ is different in the presence of the compound or signal (as compared to the absence of said compound or signal).

Cell-based screening assays can be designed by constructing cell lines in which the expression of a reporter protein, i.e. an easily assayable protein, such as β galactosidase, chloramphenicol acetyltransferase (CAT) or luciferase, is dependent on mGlu$_7$ activity. Such an assay enables the detection of compounds that directly modulate mGlu$_7$ function, such as compounds that antagonise mGlu$_7$, or compounds that inhibit or potentiate other cellular functions required for the activity of mGlu$_7$, without the requirement for complex electrophysiological analysis.

Cells suitable for the practice of the invention are preferably neural cells or other cells capable of neurotransmitter release, or of a related reporter function, which may be modulated by mGlu$_7$ as occurs in nerve endings in vivo. The cells are preferably grown in tissue culture, but alternative forms of cell culture, such as organ culture of tissue slices from chimeric or transgenic animals, may be used. In order to achieve selectivity in the screening systems of the invention, cells may be chosen which lack mGlu$_7$ in the natural state, and transfected with mGlu$_7$ DNA as set out above. Wild type cells may then be used as controls. Alternatively, the knockout technology described hereinbefore may be used selectively to delete mGlu$_7$ from cells which express this receptor in the natural state, thus generating a control cell which may be used to assess the effects of test compounds on wild-type cells.

According to a further aspect of the invention, there is provided the use of an antagonist of mGlu$_7$ for selectively reducing short-term potentiation (STP) of neural synapse without affecting long-term potentiation (LTP). The observation is that the stable level of LTP generated is not directly related to the initial level of STP is surprising. Treatments which affect tetanus-induced synaptic potentiation generally either depress STP and LTP in parallel or, like many protein kinase inhibitors and targeted deletions of protein kinase genes, selectively block LTP. This has led to the belief that STP and LTP are serial processes where STP is required for, but does not necessarily lead to, LTP (Hanse, E. & Gustafsson, B. (1994) *Neurosci. Res.* 20:15–25). As set forth herein, this does not appear to be the case, since STP can be reduced without affecting LTP. Thus, STP and LTP appear to be separable parallel, rather than serial, phenomena.

The capability of a synapse to adjust the level of STP without affecting the ensuing LTP adds greater flexibility to synaptic plasticity. Without activation of mGlu$_7$ the change in synaptic efficiency shows little decrement with time and is readily saturable. Activation of mGlu$_7$ adds a transient and more robust component to information storage which could be important for short-term memory. Accordingly, the invention also provides the use of an mGlu$_7$ agonist in the manufacture of a composition for the treatment of short-term memory disorders. The invention is further described hereinbelow, for the purposes of illustration only, in the following Examples.

EXAMPLE 1

Construction of mGlu$_7^{-/-}$ Mice

A genomic fragment containing the first coding exon of the mouse mGlu$_7$ gene is isolated from a 129SV/J lambda FIX phage library (Stratagene), probed with a human mGlu$_7$ cDNA. A 2.055 kb NheI-NheI DNA fragment comprising this exon is sequenced. The first coding exon contains at least 405 bp of 5' untranslated region (UTR; as judged by homology to rat mGlu$_7$ cDNA), followed by codons for the first 164 amino acids of mouse mGlu$_7$. The targeting vector is constructed by inserting a 0.6 kb NruI-XhoI DNA fragment (comprising 115 bp of 5' UTR) 5' of the pMCNeo cassette into a StuI-XhoI cleaved pTV-0 vector. A 7 kb NheI-NheI DNA fragment comprising mGlu$_7$ genomic sequences downstream of the 2.055 kb Nhe I-Nhe I fragment is inserted into a NheI site located in between the pMCNeo and the pMCTK cassette of pTV-0. E14 ES cells (129/Ola; genotype A$^w$(agouti), c$^{ch}$(Albino), p(pinked-eyed dilution), are transfected with 30 µg of NotI-linearized and ddXTP-end-filled (using Klenow enzyme) targeting vector by electroporation (Biorad Gene Pulser; 250V and 500 µF). G418 (600 µg/ml) and Ganciclovir (Gancv; 2 µM) selection are applied 24 and 48 h later, respectively. Genomic DNA from double-resistant ES colonies is subjected to PCR analysis using either one of two PCR primers matching sequences in the NheI-NruI fragment located just 5' but not contained within the targeting vector (primer-1, 5'-CTTCTGCCAGAGCTGACAGTCAAAG-3', SEQ ID NO. 1; primer-2, 5'-GTCAGCACCAATATCGCGACTCATC-3', SEQ ID NO. 2), and either one of two primers located in the neo gene primer-3, (5'-GCGTGCAATCCATCTTGTTCAATGG-3', SEQ ID NO. 3; primer4, 5'-GCGCTGACAGCCGGAACACG-3', SEQ ID NO.4). Combinations of primer-1 or -2 and either one of two primers matching sequences in the coding region of the first coding exon (primer-5, 5'-GAAAGTGAGCGACTGTTCGAGCG-3', SEQ ID NO.5; primer-6, 5'-GATGTTGGCTACCATGATGGAGACCG-3', SEQ ID NO.6) serve to detect the presence of a wild-type mGlu$_7$ allele. Two out of 112 G418$^r$ Gancv$^r$ double-resistant ES cell clones carried a correctly targeted mGlu$_7$ allele, as assessed by PCR and confirmed by Southern blot analysis of genomic DNA digested with NheI and NcoI, respectively, and probed with probe A (158 bp NheI-NruI fragment), probe B (0.6 kb NruI-XhoI fragment) and a neo gene probe (probe D). Southern analysis using a complete mGlu$_7$ cDNA probe (probe D) detecting all mGlu$_7$ exons reveals no additional rearrangements in the locus. Wild-type (+) and mutant alleles (−) are indicated by the presence of a 2 kb (+) versus 1.8 kb (−) NheI and a 2.5 kb (+). versus a 2.3 kb (−) NcoI DNA fragment when probed with probe A or B (FIG. 1). The diagnostic sizes for a properly targeted mGlu$_7$ allele when probed with neo (probe D) are 1.8 kb (NheI) and 2.3 kb (NcoI). Both ES clones are used successfully to produce chimeric mice (11 for each clone) by aggregation for 2–3 h with 10$^6$ ES cells/ml. Several germ-line chimeras are obtained from each clone. F1 mice carrying a targeted mGlu$_7$ allele are identified by Southern blot analysis. F2 mice, derived from matings of pairs of heterozygous parents, are screened by PCR using pairs of primer-1 and 3 or 4 to detect the targeted allele, and primer-7 (5'-GAGAGATGGATAGCAAGCAAGGGAG-3', SEQ ID NO.7) and primer-8 (5'-GTGTCCCTGGAACAAGTGTCCAG-3', SEQ ID NO.8) to detect the endogenous mGlu$_7$ allele in mGlu$_7^{+/+}$ and $^{+/-}$ mice, and confirm its absence in mGlu$_7^{-/-}$ mice. Southern and Northern blot analysis, sequencing, PCR and RT-PCR are performed according to standard protocols. RT-PCR of mGlu$_7^{+/+}$ and $^{-/-}$ brain RNA is performed using several pairs of oligonucleotide primers, including primer-1 and -4, primer-1 and -10, primer-11 and -10, and primer-9 and -10. Primer-9 and -10 are specifically designed to detect sequences comprising exon-b (92 bp), encoding one of two (a and b) C-terminal splice variants of mGlu$_7$. No RT-PCR products are detected using mGlu$_7^{-/-}$ brain as template and primer 11+10 or 9+10 whereas expected products of 2.7 kb and 0.092 kb are readily detected using mGlu$_7^{+/+}$ RNA.

According to the foregoing protocol, therefore, the mGlu$_7$ gene is inactivated in E14 (129/Ola) embryonic stem cells by insertion of a neo cassette replacing 0.585 kilobases (kb) of the first coding exon and 0.73 kb of the following intron (FIG. 1). The inactivated gene is identified by Southern blotting and PCR analysis. No mGlu$_7$ mRNA can be detected in mGlu$_7^{-/-}$ (mutant) mice by Northern blot analysis or reverse-transcriptase PCR of brain RNA. Reduced levels of mGlu$_7$ mRNA are present in brains of mGlu$_7^{+/-}$ mice. Potential compensatory gene-regulatory mechanisms, such as an altered expression of mGlu$_4$ and mGlu$_8$, are not detected in mGlu$_7^{-/-}$ mice, neither at the mRNA nor at the protein level. mGlu$_7$ protein is absent in mGlu$_7^{-/-}$ brain as shown by immunoblotting and immunocytochemistry. Histological analysis did not reveal any gross anatomical abnormalities in the hippocampus or elsewhere in the brain of mGlu$_7^{-/-}$ mice. Behaviourally, young adult mGlu$_7^{-/-}$ mice appear to be normal and mutant mice experience no major morbidity.

EXAMPLE 2

Characterisation of mGluR7−/− Mice

To investigate the possible functions of mGlu$_7$ electrophysiological experiments are performed in the CA1 region of the hippocampus, a region rich in mGlu$_7$. Although no selective mGlu$_7$ agonists are known, high concentrations of L-AP4 (e.g., 1 mM) can activate mGlu$_7$ in recombinant systems (Okamoto, et al., (1994) *J Biol. Chem.* 269:1231–1236; Saugstad, et al., (1994) *Mol Pharmacol* 45:367–372). It has been shown that 1 mM L-AP4 can depress synaptic transmission in the Schaffer collateral-commissural pathway and this effect has been attributed to the activation of mGlu$_7$ (Gereau, R. W. & Conn, P. J. (1995) *J. Neurosci.* 15:6879–6889; Manzoni, O. & Bockaert, J. (1995) *Eur. J. Neurosci.* 7:2518–2523). L-AP4 (1 mM) is therefore applied to wild-type and mGlu$_7^{-/-}$ mice. Three patterns are seen; a large and slowly reversible depression, a more modest depression which does not fully reverse and is associated with oscillations in the size of the synaptic response, and no effect. However, all three patterns are seen in both wild-type and mutant mice. On average there is no significance difference in the actions of L-AP4 between groups; the peak L-AP4 induced depressions for wild-type and mutant mice are 40±10% (n=15) and 33±10% (n=14), respectively (P>0.05). Furthermore, no statistically significant differences are seen in intrinsic or synaptic properties between wild-type and mutant mice. Also, paired-pulse facilitation is similar between both groups. Thus, the facilitation ratio obtained, using an interpulse interval of 50 ms, is 1.49±0.03 and 1.45±0.04 for wild-type (n=9) and mutant (n=9) mice, respectively (P>0.05).

Since certain members of the mGlu family have been implicated in the generation of LTP in area CA1, the ability of wild-type and mutant mice to support this form of synaptic plasticity is compared as follows. 400 µm thick slices are prepared from the hippocampi of 5–10 week old mutant mice and littermate wildtypes using standard procedures. Slices are submerged in a medium which comprises (mM): NaCl 124; KCl 3; NaHCO$_3$ 26; NaH$_2$PO$_4$ 1.4; MgSO$_4$ 1; CaCl$_2$ 2; D-glucose 10; (bubbled with 95% O$_2$/5% CO$_2$; pH 7.4), and is perfused at a rate of approximately 4 ml. min$^{-1}$ (29–31° C.). Extracellular recordings are obtained from stratum radiatum of area CA1 in response to low frequency (0.033 Hz) stimulation of the Schaffer collateral-commissural pathway. Measurements of the slope of the field EPSP are used throughout.

There are no apparent differences in low frequency synaptic transmission between the two groups of mice. For example, the maximal slope of field EPSPs for wild-type (n=14) and mutant mice (n=12) are 0.34±0.04 and 0.40±0.07 V.s$^{-1}$ when evoked using stimulus intensities (10.7±0.8 and 9.9±0.5 V, respectively) which produces responses set to be 40% of the size where a population spike is first detectable. Tetanic stimulation (100 Hz, 1 s, test intensity) is delivered at the times indicated by arrows. For each protocol, one slice is used per animal, hence n values give the number of slices/mice used. Statistical significance is determined using a repeated measures ANOVA test and unpaired Students t-tests. Animals are genotyped by PCR and presented to the experimenter in a randomised and blind manner.

Tetanic stimulation induces LTP in both groups of mice. The level of LTP, measured at 60 min following tetanic stimulation, is not significantly different between groups (the respective values for wild-type and mutant mice are 35±7% (n=14) and 22±7% (n=12) (P>0.05). However, the initial phase of potentiation, which is commonly referred to as STP[1], is markedly reduced in the mutant mice. For example, the initial measure of potentiation, obtained between 0.5 and 2 min, for the respective groups is 163±21% (n=14) and 89±15% (n=12) (P<0.01) and the differences remained statistically different for 16 min following tetanic stimulation.

An important property of LTP is its ability to saturate following repeated tetanisation. Therefore the saturation profiles of wild-type and mutant mice is compared. In wild-types, LTP is readily saturated but STP is relatively resistant to saturation (n=4). Since in mutants, STP is greatly reduced the saturation profiles are very distinct, with most of the capacity for potentiation being utilised by a single tetanus (n=5).

To determine whether the L-glutamate released by tetanic stimulation has an acute action on the level of synaptic transmission via its interaction with mGlu$_7$ additional experiments are performed, following the saturation of LTP. Twenty shocks delivered at 100 Hz are followed by a test pulse delivered either 50 ms or 500 ms later. During the high frequency train the size of individual AMPA receptor-mediated EPSPs increased and then decreased in both groups. However, from approximately 50 ms into the train, the EPSPs are smaller, relative to the first EPSP of the train, in the mutant mice. The post-tetanic response, assessed as the ratio of the test EPSP to the first EPSP in the train, is also reduced in the mutant; the ratios obtained, using respective interpulse intervals of 50 ms and 500 ms, were 2.16±0.01 and 0.88±0.07 for wild-type (n=8) and 1.43±0.11 and 0.65±0.05 for mutant (n=8) mice (P<0.05). In addition to changes in EPSPs, there was also a reduction in the size of summated IPSPs during and following the train in mutant mice.

The present results show that mGlu$_7$, a member of subgroup III mGluRs, has a very distinct role in tetanus-induced synaptic potentiation; its presence influences the level of STP but not the stable level of LTP generated. In contrast, members of group I mGlus (mGlu$_1$ and mGlu$_5$) are involved, in complex ways, in the generation of LTP but not STP. The latter group couple to phospholipase C where they can affect intracellular Ca$^{2+}$ signalling and the activation of PKC. Group III mGlus couple negatively to adenylyl cyclase in expression systems, but the coupling mechanisms of mGlu$_7$ in native systems is unknown. Whatever its coupling mechanisms, the present data indicate that mGlu$_7$ can be activated synaptically to positively influence the level of synaptic glutamate release within tens of milliseconds and that this action lasts for many minutes.

EXAMPLE 3 mGluR7−/− Mice are Susceptible to Epiletic Seizures

When mGluR7−/− mice over approximately 12 weeks of age are transferred to a new cage with fresh sawdust, we have observed that a sensory stimulus, the identity of which is being investigated, results in spontaneous seizures. The epileptic phenotype becomes detectable around three months of age (in mice with a mixed C57BI/6×129Sv/Ola genotype), is sex-independent, and is not seen in mGluR7+/− and mGluR7+/+ age-matched animals and/or littermates. The seizures in mGluR7−/− mice are clonic-like, of different severity, and sometimes accompanied by running and, occasionally, death. After experiencing seizures, the mice show a lag phase (of variable duration up to several days) before a subsequent seizure episode can be triggered using sensory stimulation. When re-tested after 7 days without a stimulus, 20 out of 20 mGluR7−/− mice (sex mixed) displayed again seizure activity using following the stimulus. The epileptic phenotype observed after sensory stimulation can not be explained by gross and obvious abnormalities in the EEG (electroencephalogram). When not exposed to a particular sensory stimulus, spontaneous seizure activity was not detected in EEG recordings taken continuously for 48 hours from mGluR7−/− mice. The spontaneous seizures triggered by a sensory stimulus following transfer into a new cage occurred in mGluR7 knockout mice derived from two independently targeted ES cells clones indicating that the phenotype is not caused by a mutation, unrelated to the mGluR7 knockout gene, and introduced while manipulating the ES cells.

EXAMPLE 4

Pentylenetetrazol (PTZ)-induced Seizures in mGluR7−/− Mice

Intraperitoneal (i.p.) injection of a normally subconvulsive dose of PTZ (40 mg/kg) induced seizures in 9 out of 9 homozygous mGluR7 knockout mice (age 9 months) as shown in the Table below. None of 9 wild type mice (mGluR7+/+) showed seizures and only 1 out of 9 mGluR7+/− mice had some clonic seizures.

| mGluR7 −/− (= homozygous knockout mice) | | | | |
| --- | --- | --- | --- | --- |
| Animal Nr. | weight sex | Clonic activity | Tonic activity | Exitus |
| 1 | 30 g f | 2' | 12' | 12' |
| 2 | 28 g f |  | 2' | 11' |
| 4 | 24 g f | 15' |  |  |
| 5 | 30 g f |  | 4' | 4' |
| 6 | 25 g f |  |  |  |
| 7 | 27 g m |  | 6' | 6' |
| 8 | 30 g m |  | 3' |  |
| 9 | 30 g m |  | 3' | 4' |
| mGluR7 +/−(= Heterozygote mice) | | | | |
| Animal Nr. | weight sex | Clonic activity | Tonic activity | Exitus |

-continued

| | | | |
|---|---|---|---|
| 1 | 24 g f | | |
| 2 | 25 g f | | |
| 3 | 24 g f | 3' | |
| 4 | 25 g f | | |
| 5 | 25 g f | | |
| 6 | 28 g f | | |
| 7 | 24 g f | | |
| 8 | 25 g f | | |
| 9 | 25 g f | | | wild-type non transgenic mice

| Animal Nr. | weight sex | Clonic activity | Tonic activity | Exitus |
|---|---|---|---|---|
| 1 | 24 g m | | | |
| 2 | 25 g m | | | |
| 3 | 24 g m | | | |
| 4 | 25 g m | | | |
| 5 | 25 g m | | | |
| 6 | 28 g m | | | |
| 7 | 24 g m | | | |
| 8 | 25 g m | | | |
| 9 | 25 g m | | | | m = male; f = female

In addition, two mGluR7−/− and two mGluR7+/− mice were equipped with surface electrodes to record EEGs before and after injection of 40 mg/kg PTZ. EEG recordings before PTZ injection showed no abnormalities, either in the homozygous mice or the heterozygous mice as compared to EEGs recorded from non-transgenic mice. Following injection of 40 mg/kg PTZ, the EEGs recorded from homozygous mGluR7 knockout mice showed typical signals reminiscent of seizure activity. In contrast, no such activity developed in mGluR7+/− mice.

Thus, mGluR7−/− but not mGluR7+/− mice develop a phenotype that includes an increased vulnerability for seizures triggered by a sensory stimulus or a subconvulsive dosis of a drug, in this case examplified by PTZ at 40 mg/kg.

This sensitivity to a subconvulsive dose of PTZ is not yet evident at age 6 weeks but clearly evident at age 10 weeks in mGluR7 homozygous but not in heterozygous littermates as shown in the table below.

| | mGluR7 +/− | | | mGluR7 −/− | |
|---|---|---|---|---|---|
| | Age | | | Age | |
| Animal Nr. | 6 Weeks Clonic activity | 10 Weeks Clonic activity | Animal Nr. | 6 Weeks Clonic activity | 10 Weeks Clonic activity |
| 7550 | | | 7549 | | 4' |
| 7551 | | | 7553 | | 4' |
| 7552 | | | 7554 | | |
| 7560 | | | 7555 | | |
| 7561 | | | 7556 | | 2' |
| 7562 | | | 7557 | | 4' |
| 7563 | | | 7559 | 6' | ∅ |
| 7566 | | | 7564 | | 4' |
| | | | 7565 | | 2' |
| | | | 7570 | | |

Also in these experiments, wild type non-transgenic mice were tested in parallel and shown to have no seizures following i.p. injection of 40 mg/kg PTZ.

∅=Animal Nr. 7559 was sacrificed after it developed the clonic seizures at 6 Weeks of age.

What is claimed is:

1. A transgenic mouse homozygous for an inactivated endogenous mGlu7 gene, exhibiting symptoms of epileptic seizures.

2. A method for screening a compound or a mixture of compounds for mGlu7 agonist or antagonist activity, comprising the steps of; exposing a transgenic mouse and an mGlu7-expressing mouse to the compound or mixture of compounds wherein said transgenic mouse is homozygous for an inactivated endogenous mGlu7 gene and exhibits symptoms of epileptic seizures, evaluating the mice for susceptibility to epileptic seizures, and comparing the effect of the compound or mixture of compounds in the transgenic mouse to the effect of the compound or mixture of compounds in an mGlu7 expressing mouse to thereby determine if the compound or mixture of compounds has agonist or antagonist activity.

3. The method according to claim 2 wherein the effect of the compound or mixture of compounds is assessed by observing the behavioral effect thereof on the mice.

4. The method according to claim 2 wherein the effect of the compound or mixture of compounds is assessed by electrophysiological measurement of neural activity.

* * * * *